(12) United States Patent
Mercurio et al.

(10) Patent No.: US 7,405,242 B2
(45) Date of Patent: *Jul. 29, 2008

(54) AEROSOL DELIVERY SYSTEMS

(75) Inventors: Anthony Fred Mercurio, Rivervale, NJ (US); Derek Alfred Wheeler, Guildford (GB)

(73) Assignee: Drug Delivery Solutions Limited, Surrey (GB)

( * ) Notice: Subject to any disclaimer, the term of this patent is extended or adjusted under 35 U.S.C. 154(b) by 537 days.

This patent is subject to a terminal disclaimer.

(21) Appl. No.: 10/702,041

(22) Filed: Nov. 6, 2003

(65) Prior Publication Data

US 2004/0132831 A1  Jul. 8, 2004

Related U.S. Application Data

(63) Continuation-in-part of application No. 10/288,590, filed on Nov. 6, 2002, now Pat. No. 7,053,124.

(51) Int. Cl.
*C09K 3/30* (2006.01)
*A61K 8/00* (2006.01)

(52) U.S. Cl. .............................. 516/8.1; 516/6; 516/8; 424/401; 424/45; 424/47; 514/945

(58) Field of Classification Search .................. 516/6, 516/8, 8.1; 424/401, 45, 47; 514/945
See application file for complete search history.

(56) References Cited

U.S. PATENT DOCUMENTS

| 4,486,333 | A | * | 12/1984 | Sebba | 516/14 |
|---|---|---|---|---|---|
| 4,810,407 | A | * | 3/1989 | Sandvick | 516/DIG. 1 |
| 4,999,198 | A | * | 3/1991 | Barnett et al. | 424/449 |
| 5,849,838 | A | * | 12/1998 | Barlow | 524/804 |
| 6,165,479 | A | * | 12/2000 | Wheeler | 424/400 |
| 6,652,632 | B2 | * | 11/2003 | Moodycliffe et al. | 106/3 |
| 6,749,673 | B2 | * | 6/2004 | Moodycliffe et al. | 106/3 |
| 6,881,757 | B2 | * | 4/2005 | Moodycliffe et al. | 516/6 |
| 2002/0058055 | A1 | * | 5/2002 | Zecchino et al. | 424/401 |
| 2004/0002550 | A1 | * | 1/2004 | Mercurio | 516/10 |
| 2004/0087667 | A1 | * | 5/2004 | Mercurio | 516/77 |
| 2004/0091427 | A1 | * | 5/2004 | Moodycliffe et al. | 424/45 |
| 2004/0116544 | A1 | * | 6/2004 | Mercurio | 516/77 |
| 2004/0132831 | A1 | * | 7/2004 | Mercurio et al. | 516/6 |

* cited by examiner

*Primary Examiner*—Daniel S Metzmaier
(74) *Attorney, Agent, or Firm*—Dykema Gossett PLLC

(57) ABSTRACT

An aerosol composition which is prepared from a biliquid foam, an aqueous phase and a propellant, and wherein an oil soluble functional material is incorporated into the biliquid foam during preparation to enable this material to be more readily incorporated into the composition. The aerosol composition can be contained in a pressurized aerosol can and can be a polish, an air freshener, a repellant, a pre- or post-shave preparation, a shaving preparation or a follicle softener.

2 Claims, No Drawings

AEROSOL DELIVERY SYSTEMS

The present application is a continuation-in-part of application Ser. No. 10/288,590, filed Nov. 6, 2002, the priority of which is hereby claimed and is now U.S. Pat. No. 7,053,124.

The present invention relates to aerosol delivery systems and, in particular, to aerosol delivery systems which are designed to reduce the amount of surfactant included therein.

Aerosol compositions are known in the art which contain oil soluble functional materials such as fragrances, silicones, esters and bio-active materials therein. In order to disperse the oil soluble functional material into the aqueous phase of the aerosol composition there is generally a requirement to include in the composition from two to three times by weight of the functional material of a solvent or surfactant therein.

We have now found that incorporation of the oil soluble functional material into a biliquid foam enables this material to be readily dispersed throughout the aqueous phase of the aerosol composition without the use of excessive amounts of solvents or surfactants, which may affect the material and which may neutralize the effects of any preservatives contained within the aerosol composition.

Accordingly, the present invention provides an aerosol composition which is prepared from a biliquid foam, an aqueous phase and a propellant.

The invention also provides a pressurized aerosol can comprising an aerosol composition of the invention.

The invention also provides a process for preparing an aerosol composition of the invention which comprises adding the aqueous phase to a vessel, adding the biliquid foam to the vessel and mixing and filling an aerosol can with the addition of a suitable propellant.

Biliquid foams are known in the art and are described in the following literature references by Sebba: "Biliquid foams", J. Colloid and Interface Science, 40 (1972) 468-474; and "The Behaviour of Minute Oil Droplets Encapsulated in a Water Film", Colloid Polymer Sciences, 257 (1979) 392-396.

U.S. Pat. No. 4,486,333 to Sebba describes a particular method for the preparation of biliquid foams by agitating a hydrogen bonded liquid containing a soluble surfactant to produce a gas foam and intermittently adding to the gas foam a non-polar liquid which is immiscible with the hydrogen bonded liquid, the surfactant-containing hydrogen bonded liquid being selected to provide a spreading coefficient equal to or greater than zero.

The biliquid foam which is incorporated into the aerosol compositions of the present invention generally contains at least one oil soluble functional material therein. Examples of the oil soluble functional materials are fragrances, lubricants, vegetable oils, fuels, silicones, esters and bioactive materials.

The biliquid foam which is used in the present invention will preferably comprise from 70 to 95% by weight of the oil phase, which may consist solely of the oil soluble functional material, and 5 to 30% by weight of the continuous phase, which is preferably an aqueous phase. A surfactant to stabilise the biliquid foam may also be included in an amount of from 0.1 to 3%, preferably 0.1 to 1% by weight based on the total weight of the formulation. Suitable surfactants are, for example, sodium lauryl ether sulphates, polyethoxylated castor oil, ethoxylated oleyl alcohols or polyethoxylated hydrogenated castor oils.

Propellants which are used in aerosol delivery systems are well known in the art and will preferably be liquified petroleum gas (LPG), which is preferably butane, optionally in admixture with propane. The propellant will generally be present in an amount of from 5 to 40% by weight.

The aerosol compositions of the present invention will generally include the biliquid foam in an amount of from 0.1 to 10% by weight. The biliquid foam will therefore generally provide the desired oil soluble functional material in an amount of from 0.07 to 9.5% by weight.

The invention includes within its scope an aerosol composition which comprises from 0.01 to 40% by weight of the biliquid foam, from 5 to 40% weight of the propellant and from 20 to 95% by weight of water.

The aqueous phase of the aerosol composition may include therein one or more surfactants or other additives. The surfactant may be chosen to prevent interaction of the propellant with the biliquid foam. Cationic surfactants are preferred, in particular quaternary ammonium compounds or amine oxides. Surfactants may also be chosen to create an affinity with the propellant.

The aerosol compositions of the present invention may be packaged in cans which are well known in the art and generally are formed of aluminium or lacquered or unlacquered tin plate or the like.

Methods of producing biliquid foams are described in U.S. Pat. No. 4,486,333 involving the preliminary formation of a gas foam in order to provide a sufficiently large surface area on which the biliquid foam can subsequently be formed. It has been found that the prior formation of a gas foam is not required to manufacture a stable biliquid foam, provided that a suitable stirring mechanism is provided in the manufacturing vessel.

Such an apparatus comprises a tank provided with a stirrer in which the stirrer blade breaks the interface between the liquid and air and provides low shear mixing throughout the whole of the volume of the biliquid foam throughout the whole of the production process. A delivery device is provided through which the oil phase (non-polar liquid), which will comprise the internal phase of the dispersion is delivered to the tank. The design of the delivery device is such that the rate of addition of the internal phase fluid can be controlled and varied during the production process. A feature of the production process is that the internal (oil) phase is added to the stirred aqueous phase slowly at first until sufficient droplets have been formed to constitute a large, additional surface area for the more rapid formation of new droplets. At this point, the rate of addition of the oil phase may be increased.

The production process consists of the following steps:

1. The addition of one or more chosen surfactants to one or other or both phases (as previously determined by experiment).
2. The charging of the aqueous phase into the bottom of a process vessel.
3. The incorporation of the stirrer into the vessel so that it stirs the surface of the aqueous phase.
4. Adjustment of the stirrer speed to a previously determined level.
5. The slow addition of the internal phase whilst continuing to stir at the prescribed speed.
6. The speeding up of the rate of addition of the oil phase once a prescribed amount (usually between 5% and 10% of the total amount to be added) has been added.

The stirring rate and the rate of addition of the oil phase are variables, the values of which depend upon the detailed design of the manufacturing plant (in particular, the ratio of tank diameter to impeller diameter), the physico-chemical properties of the oil phase and the nature and concentrations of the chosen surfactants. These can all be pre-determined by laboratory or pilot plant experiment.

It will be understood by those skilled in the art that other manufacturing methods for the biliquid foam may be used, as appropriate.

The preparation of the biliquid foams proceeds independently of the preparation of the final aerosol compositions of the invention. The aerosol compositions may be prepared by adding the aqueous phase, optionally including one or more surfactants therein to a suitable vessel, adding the biliquid foam thereto and mixing. The composition so prepared is then filled into aerosol cans using techniques known in the art. The compositions are then pressurized in the aerosol cans, with the addition of a suitable propellant, using techniques known in the art.

The aerosol compositions of the present invention will generally possess one or more of the following advantages:
- the elimination of the need for the use of large amounts of solvents or surfactants and volatile organic compounds.
- the potential to reduce skin irritation in compositions which are to be applied to the skin;
- the possibility to include in the composition oils which would generally be incompatible with one another;
- the possibility of using lower levels of fragrance components, whilst obtaining the same level of fragrance impact.
- the possibility of using lower levels of preservatives, whilst obtaining the same level of preservation.
- better performing formulations which allow dispensing using less propellant to achieve similar results.

The aerosol compositions of the invention are preferably used as or in polishes, particular furniture polishes, air fresheners, fragrances/moisturisers, sunscreens, shaving preparations or follicle softeners.

The aerosol compositions of the invention may contain other components (in addition to the biliquid foam, aqueous phase and propellant) depending upon the uses to which they are to be put. Thus, where the aerosol compositions are to be used as polishes, the compositions may additionally contain waxes, for example vegetable waxes (for example, carnauba and candelilla), optionally combined with one or more softeners, for fillers and pigments. One or more alcohols or other solvents may also be present.

Where the aerosol compositions are used as furniture polishes, these may additionally contain one or more of silicone red oil, lemon oil and petroleum solvent; nail polishes generally comprise nitrocellulose, optionally with amyl acetate solvent present.

Where the aerosol compositions are used as air fresheners, a perfumed component (e.g. a free perfume) will generally be present. In addition, such compositions may comprise one or more of the group comprising porosity modifiers, disintegrants, water-swelling agents and colourants. Also present may be inert fillers, hygroscopic agents, binders, coating materials and moisture-providing agents.

Where the compositions are used as repellents, these will generally comprise an active repellent agent such as citronella oil, dimethyl phthalate, n-butylmesityl oxide oxalate and 2-ethyl hexane-1,3-diol. Actidione may be used as an active agent in rodent repellents as may thiuram disulfide, amino complexes with trinitrobenzene and hexachlorophene.

Where the aerosol compositions are used as shaving preparations, appropriate additional components may be as described in *Harry's Cosmeticology*, 7th Ed., J. B. Wilkinson and R. J. Moore (editors), Chemical Publishers, New York, 1982, pp. 126-189.

Sunscreens will generally comprise either of both of both a UV-A or UV-B filter. UV-A filters are generally derivates of dibenzoylmethane, particularly avobenzone (4-(1,1-dimethylethyl)-4'-methoxydibenzoylmethane, sold under the brand name PARSOL 1789). Preferably, each of auobenzone, octyl salicylate and oxybenzone is present. Other diabenzolymethane derivatives known to be UV-A filters are described in U.S. Pat. Nos. 4,387,089, 4,489,057 and 4,562,067. UV-B filters are generally paramethoxycinnamic acid esters, such as 2-ethylhexyl paramethoxycinnamate, generally known as octyl methoxy cinnamate or PARSOL MCX, octyl salicylate and oxybenzone.

Follicle softeners generally comprise one or more of the following: surfactants, lubricants, humectants, foaming agents, fragrances, fatty acids and bases.

The contents of all publications referred to herein are hereby incorporated by reference.

The present invention will be further described with reference to the following Examples.

EXAMPLE 1

Preparation of Biliquid Foam

A biliquid foam was prepared from the following ingredients using the stirring method as described above. The aqueous phase was introduced into a beaker equipped with a stirrer, the diameter of which was approximately 80% of the beaker diameter and the depth sufficient to provide mixing throughout the body of the biliquid foam once the oil addition was complete, to provide low shear mixing. The fragrance and surfactant were slowly added over a period of a few minutes with stirring continuing after completion of the oil addition until the sample became homogeneous.

| Oil Phase | % w/w |
|---|---|
| Fragrance | 89.1 |
| Castor oil/Polyoxyethylene glycol (35) adduct (Etocas 35 NF) | 0.9 |

| Aqueous Phase | |
|---|---|
| Demin. water | 9.90 |
| Sodium lauryl ether sulphate (Standopol) | 0.10 |
| | 100.00 |

Preparation of Screening Aerosol Composition

An aerosol formulation was prepared from the following ingredients:

| | % w/w |
|---|---|
| Biliquid foam | 0.34 |
| Polyquaternium-11 (Gafquat 755N) | 5.00 |
| Isopentane | 5.00 |
| Water | 89.66 |
| | 100.00 |

The water was mixed with the polyquaternium-11 and the biliquid foam added. The isopentane was then added to the mixture. The mixture demonstrated the suitability of the invention for formulation as an aerosol composition using a suitable propellant to replace the isopentane.

EXAMPLE 2

A screening aerosol formulation was prepared from the following ingredients:

|  | % w/w |
|---|---|
| Biliquid foam of Example 1 | 0.34 |
| Polyquaternium-11 (Gafquat 755N) | 0.10 |
| Isopentane | 5.00 |
| Water | 94.56 |
|  | 100.00 |

The water was mixed with the polyquaternium-11 and the biliquid foam added. The isopentane was then added to the mixture.

EXAMPLE 3

A screening aerosol formulation was prepared from the following ingredients;

|  | % w/w |
|---|---|
| Biliquid foam of Example 1 | 0.34 |
| Polyquaternium-11 (Gafquat 755N) | 0.05 |
| Isopentane | 5.00 |
| Water | 94.61 |
|  | 100.00 |

The water was mixed with the polyquaternium-11 and the biliquid foam added. The isopentane was then added to the mixture.

EXAMPLE 4

A screening aerosol formulation was prepared from the following ingredients.

|  | % w/w |
|---|---|
| Biliquid foam of Example 1 | 0.34 |
| Polyquaternium-7 (Mackernium 007) | 0.10 |
| Isopentane | 5.00 |
| Water | 94.56 |
|  | 100.00 |

The water was mixed with the polyquaternium-11 and the biliquid foam added. The isopentane was then added to the mixture.

EXAMPLE 5

A screening aerosol formulation was prepared from the following ingredients:

|  | % w/w |
|---|---|
| Biliquid foam of Example 1 | 0.34 |
| Dicetyl Dimonium Chloride (Proquat 868-P) | 0.10 |
| Isopentane | 5.00 |
| Water | 94.56 |
|  | 100.00 |

The water was mixed with the polyquaternium-11 and the biliquid foam added. The isopentane was then added to the mixture.

EXAMPLE 6

A screening aerosol formulation was prepared from the following ingredients:

|  | % w/w |
|---|---|
| Biliquid foam of Example 1 | 0.34 |
| Amine oxide (AO-455) | 0.10 |
| Isopentane | 5.00 |
| Water | 96.54 |
|  | 100.00 |

The water was mixed with the polyquaternium-11 and the biliquid foam added. The isopentane was then added to the mixture.

EXAMPLE 7

A screening aerosol formulation was prepared from the following ingredients:

|  | % w/w |
|---|---|
| Biliquid foam of Example 1 | 0.34 |
| Amine oxide (AO-455) | 0.05 |
| Isopentane | 5.00 |
| Water | 94.61 |
|  | 100.00 |

The water was mixed with the polyquaternium-11 and the biliquid foam added. The isopentane was then added to the mixture.

EXAMPLE 8

A screening aerosol formulation was prepared from the following ingredients:

|  | % w/w |
|---|---|
| Biliquid foam of Example 1 | 0.34 |
| Vinyl caprolactam/PVP/Dimethyl-aminomethyl methacrylate copolymer | 0.10 |
| Isopentane | 5.00 |
| Water | 94.56 |
|  | 100.00 |

The water was mixed with the polyquaternium-11 and the biliquid foam added. The isopentane was then added to the mixture.

EXAMPLE 9

A screening aerosol formulation was prepared from the following ingredients:

| | % w/w |
|---|---|
| Biliquid foam | 0.34 |
| Dimethyl lauryl amine oxide | 0.10 |
| Isopentane | 5.00 |
| Water | 94.56 |
| | 100.00 |

The water was mixed with the polyquaternium-11 and the biliquid foam added. The isopentane was then added to the mixture.

EXAMPLE 10

A screening aerosol formulation was prepared from the following ingredients:

| | % w/w |
|---|---|
| Biliquid foam | 0.34 |
| Cocamidopropylamine oxide | 0.10 |
| Isopentane | 5.00 |
| Water | 94.56 |
| | 100.00 |

The water was mixed with the polyquaternium-11 and the biliquid foam added. The isopentane was then added to the mixture.

In a similar manner to the preceding examples, further examples of aerosol compositions according to the invention are prepared from the following components:

EXAMPLE 11

Furniture Polish

| | % w/w |
|---|---|
| Mineral Oil | 21.02 |
| Deodorized Mineral Spirits | 1.20 |
| Silicone | 4.50 |
| Laureth-4 | 0.27 |
| Sodium Lauryl Ether Sulfate | 0.30 |
| Preservative | 0.05 |
| Water | 71.76 |
| Carbomer | 0.56 |
| Triethanolamine | 0.34 |

EXAMPLE 12

Fragrance/Moisturizer

| | % w/w |
|---|---|
| Water | 55.264 |
| Denatured Alcohol | 20.00 |

-continued

| | % w/w |
|---|---|
| Glycerin | 2.00 |
| Polyacrylamide and C13–14 Isoparaffin and Laureth-7 | 0.60 |
| Nylon-12 | 0.50 |
| Titanium Dioxide | 0.40 |
| Glyceryl Trioctanoate | 5.00 |
| Isododecane | 4.00 |
| Silicone | 6.00 |
| Fragrance | 6.00 |
| PEG 25 Hydrogenated Castor Oil | 0.106 |
| PEG 25 Castor Oil | 0.106 |
| Sodium Lauryl Ether Sulfate | 0.024 |

EXAMPLE 13

Air Freshener

| | % w/w |
|---|---|
| Water | 97.98 |
| Carbomer | 0.60 |
| Triethanolamine | 0.30 |
| Preservative | 0.10 |
| Fragrance | 0.45 |
| Laureth-4 | 0.27 |
| Sodium Lauryl Ether Sulfate | 0.30 |

EXAMPLE 14

Sunscreen

| | % w/w |
|---|---|
| Avobenzone | 3.00 |
| Octyl Salicylate | 5.00 |
| Oxybenzone | 4.00 |
| Diethylhexyl 2.6-Naphthalate | 5.00 |
| Sunflower Oil | 2.00 |
| Cyclopentasiloxane | 2.00 |
| PEG 35 Castor Oil | 0.21 |
| Sodium Lauryl Ether Sulfate | 0.24 |
| Water | 73.00 |
| Carbomer | 0.25 |
| Triethanolamine | 0.10 |
| Propylene Glycol | 5.00 |
| Preservative | 0.20 |

The invention claimed is:

1. A pressurized aerosol can containing an aerosol composition which comprises a biliquid foam, an aqueous phase and a propellant.

2. A process for preparing an aerosol can containing an aerosol composition which comprises a biliquid foam, an aqueous phase and a propellant, and which comprises adding the aqueous phase to a vessel, adding the biliquid foam to the vessel and mixing, and filling an aerosol can with the addition of a suitable propellant.

* * * * *